United States Patent [19]

Bullard

[11] Patent Number: 4,947,829

[45] Date of Patent: Aug. 14, 1990

[54] MODULAR BLADE LARYNGOSCOPE

[76] Inventor: James R. Bullard, 707 Somerset Way, Augusta, Ga. 30909

[21] Appl. No.: 192,334

[22] Filed: May 10, 1988

[51] Int. Cl.⁵ .............................................. A61B 1/06
[52] U.S. Cl. ...................................................... 128/11
[58] Field of Search ......................... 128/10, 11, 15, 16, 128/20, 23

[56] References Cited

U.S. PATENT DOCUMENTS

| | | | |
|---|---|---|---|
| 1,246,338 | 11/1917 | Smit. | |
| 1,613,373 | 1/1927 | Beck. | |
| 1,638,986 | 8/1927 | De Zeng | 128/11 X |
| 2,354,471 | 7/1944 | Macintosh | 128/10 |
| 2,765,785 | 10/1956 | Pagoto | 128/15 |
| 3,195,536 | 7/1965 | Hovnanian et al. | 128/6 |
| 3,210,079 | 10/1965 | Tryon | 273/540 |
| 3,598,113 | 8/1971 | Moore | 128/11 |
| 3,643,654 | 2/1972 | Felbarg | 128/11 |
| 3,677,262 | 7/1972 | Zukowski | 128/6 |
| 3,766,909 | 10/1973 | Ozbey | 128/11 |
| 3,771,514 | 11/1973 | Huffman et al. | 128/11 |
| 3,776,222 | 12/1973 | Smiddy | 128/6 |
| 3,863,627 | 2/1975 | Bouffard | 128/10 |
| 3,884,222 | 5/1975 | Moore | 128/11 |
| 3,913,568 | 10/1975 | Carpenter | 128/11 |
| 4,086,919 | 5/1978 | Bullard | 128/11 |
| 4,337,761 | 7/1982 | Upsher | 128/11 |
| 4,527,553 | 7/1985 | Upsher | 128/11 |

FOREIGN PATENT DOCUMENTS 2133694 7/1984 United Kingdom ................... 128/20

OTHER PUBLICATIONS

"Multi-Purpose Anterior Commissure Larngoscopes", American V. Mueller p. 776.
Dec. 16, 1986, Official Gazette, p. 1156 Re. 32,306.
Reichert Price List, Jul. 1, 1984.
"Design Breakthrough in Laryngoscopy", by J. Roger Bullard M.D., Oct. 1985.

Primary Examiner—William H. Grieb
Attorney, Agent, or Firm—Perman & Green

[57] ABSTRACT

A laryngoscope having a blade comprising a shaft positionable proximate the tongue and upper throat regions of a patient and means for removably mounting a tongue leaf with the shaft whereby different leafs can be used with the laryngoscope.

9 Claims, 1 Drawing Sheet

MODULAR BLADE LARYNGOSCOPE

BACKGROUND OF INVENTION

1. Field of The Invention This invention relates to an instrument for accessing the laryngeal area of the human body and, more particularly, to an improved laryngoscope having a blade with a removable leaf.

2. Prior Art Laryngoscopes are widely known and used in the medical field to facilitate endotracheal intubation of a patient during surgery to provide a positive air passageway for the administration of anesthesia and/or for the mechanical ventilation of the lungs of the patient. In the human anatomy, the epiglottis normally overlies the glottis opening into the larynx to prevent the passage of food into the trachea during eating; therefore, in endotracheal intubation, it is necessary to displace the epiglottis from the glottal opening to permit the air tube to be inserted into the trachea.

Various laryngoscope constructions are known. The more widely used laryngoscopes consist of an elongate, rigid metal blade which is supportably attached to a handle and is inserted through the mouth of the patient into the pharyngeal area to displace the tongue and epiglottis and permit direct visualization of the glottis through the mouth opening. Such laryngoscopes are generally provided with a light source which is directed along the blade to illuminate the area beyond the distal end of the blade. Two general types of rigid blade constructions are the straight, or so called "Miller blade", and the slightly curved, or so called "MacIntosh blade." Curved laryngoscope blade constructions having light means to facilitate illumination of the areas of observation are described in U.S. Pat. Nos. 3,598,113; 3,643,654; 3,766,909; and 3,771,514.

The standard method for performing intubation of the trachea during surgery with rigid laryngoscope blades of the straight or slightly curved type is to place the patient in a supine position, tilt the head backwards as far as possible, and distend the lower jaw to widely open the mouth. The rigid blade is then inserted through the mouth into the throat passageway to displace the tongue and epiglottis and expose the glottis of the patient. The larynx is then viewed through the mouth opening from an observation position just above and behind the head of the patient by sighting generally along the axis of the blade. The endotracheal tube is inserted, either orally or transnasally, and passed alongside the blade through the glottis.

Surgical instruments having means for indirect illumination and visualization of the pharyngeal areas of the body are known. U.S. Pat. Nos. 3,776,222 and 3,913,568 disclose devices for endotracheal intubation which comprise flexible or articulatable tubular probes having internal fiber optics for lighting and viewing the internal areas of the body. As disclosed in said patents, the probes carry a slidably removable endotracheal tube surrounding their outer surfaces and the probe is directly inserted into the trachea to position the tube. Such devices obviously require the use of relatively large diameter endotracheal tubes in order to be carried on the tubular probe, and their use necessarily is limited to patients with sufficiently large airway passages to accommodate the combined size of the probe and endotracheal tube. Additionally, due to the flexible nature of the probes, it is difficult to manipulate the probe to displace the tongue and epiglottis to permit direct insertion of the tube into the trachea.

U.S. Pat. No. 2,354,471 by MacIntosh discloses a laryngoscope having a handle and hinged blade to facilitate the exposure of the larynx to pass an endotracheal tube. U.S. Pat. No. 3,643,654 by Felbarg discloses a laryngoscope comprised of a tubelike member adapted to be mounted on a conventional handle. U.S. Pat. No. 3,766,909 by Ozbey discloses a laryngoscope with a disposable blade and light guide. U.S. Pat. No. 4,527,553 by Upsher discloses a laryngoscope having a blade and separate handle.

However, a problem exists with the devices known in the prior art in that no device is provided for indirect illumination and visualization of the pharyngeal areas of the body which has a blade comprising a relatively fixed shaft or stem with a removable tongue petal or leaf.

A further problem exists with the devices in the prior art in that no means are provided for mounting alternative or interchangable types of tongue leafs with a laryngoscope having a relatively fixed shaft.

A further problem exists in the devices known in the prior art in that different devices having different types of blades must be used for different applications.

SUMMARY OF THE INVENTION

The foregoing problems are overcome and other advantages are provided by a laryngoscope having a blade with a removable leaf.

In accordance with one embodiment of the invention, an instrument for accessing a target area is provided comprising a shaft means positionable proximate the target area of a patient and means for removably mounting a leaf means on the shaft means whereby different leaf means can be used with the instrument.

In accordance with another embodiment of the invention a laryngoscope is provided comprising shaft means having a distal end positionable proximate the throat region of a patient; leaf means interactable with the tongue of a patient; and means for removably mounting the leaf means with the shaft means such that the leaf means is positionable proximate the shaft means distal end whereby the leaf means can be removed from the shaft means.

In accordance with one method of the invention, a method is provided of manufacturing a laryngoscope comprising the steps of providing separate leaf means and shaft means, the shaft means being positionable proximate the throat region of a patient; and providing a mounting means for removable mounting the leaf means with the shaft means whereby the leaf means can be connected to and removed from the shaft means.

BRIEF DESCRIPTION OF THE DRAWINGS

The foregoing aspects and other features of the invention are explained in the following description, taken in connection with the accompanying drawings wherein.

DETAILED DESCRIPTION OF THE INVENTION

Figure 1:
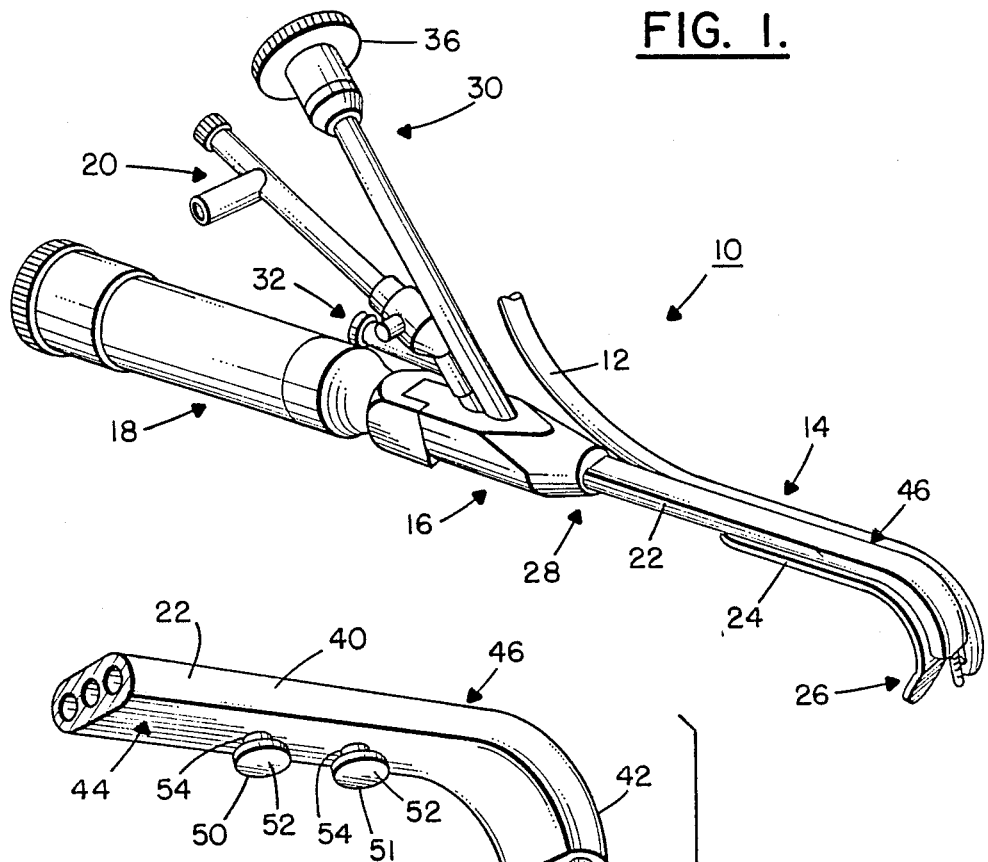
FIG. 1 is a perspective view of an instrument comprising features of the invention.

Referring to FIG. 1, there is shown a perspective view of one embodiment of the invention. In this embodiment, a laryngoscope 10 is shown intended for use for inserting an intubation or endotracheal tube 12 into the trachea of a patient. The laryngoscope 10, in this embodiment, generally comprises a blade section 14, a body section 16 and a removable handle 18. The laryngoscope shown in this embodiment comprises a placement device 20 which can grasp the leading end of the intubation tube 12, move the tube 12 relative to the laryngoscope 10 and release the tube 12 from the placement device 20 at a desired position. A full description of this placement device 20 can be found in copending U.S. patent application Ser. No. 101,834 filed Sept. 28, 1987 entitled "Improved Laryngoscope" which is incorporated in its entirety by reference herein. In the embodiment shown in FIG. 1, the laryngoscope 10 is provided with suitable means (not shown) for illuminating a target area at the distal end 26 of the laryngoscope 10 as well as suitable means (not shown) for viewing an image of the illuminated target area. The handle section 18, in this embodiment, is provided for the operator to securely hold the laryngoscope 10 and control its insertion into and removal from a patient. The handle section 18 also has an interior cavity (not shown) for retaining a power source such as dry cell batteries (not shown). The batteries communicate with a light source (not shown) in the body section 16 which provides light to a fiber optic illumination bundle (not shown) to illuminate the area adjacent the blade distal end. However, any suitable light source configuration can be used. The handle section 18, in this embodiment, is also disconnectable from the body section 16 for such occasions as cleaning or storage of the instrument 10.

The laryngoscope 10 also comprises an image viewing device 30, in this embodiment, comprising an eye piece 36, optical lenses (not shown) and a fiber optic image bundle (not shown). The image bundle (not shown) generally is positioned between the eye piece 36 and the distal end 26 such that an operator can view the area proximate the distal end of the blade section 14 by viewing the image carried by the image bundle at the eye piece 36. However, any suitable image viewing device can be used including a television camera. A secondary working channel entry port 32 is also provided at the body section 16 which communicates with a working channel (not shown) for transmitting gases to the pharyngeal area of the patient or for allowing the removal of liquids such as secretions or blood through the use of suction. The placement device 20 can be removed from the instrument 10 for these purposes.

The blade section 14 of the laryngoscope 10 generally comprises an elongate, rigid shaft or stem 22 and a removable leaf or petal 24. The blade section 14, in this embodiment, has a distal end 26 intended for leading insertion into the patient's mouth and a proximal end 28 supportably connected to the body section 16. The blade section 14, in this embodiment, has a straight configuration with a curved distal end such that a physician can insert the blade section 14 into the mouth of a patient while the patient is in a supine position. However, as will be seen below, the present invention can be used with any type of laryngoscope including laryngoscopes with anatomically curved blades.

Figure 2:
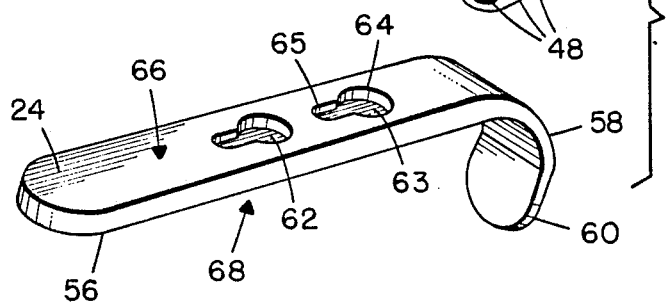
FIG. 2 is a perspective view of the separate shaft and leaf of the blade of the instrument shown in FIG. 1.

Referring now to FIG. 2, a perspective view of the separate shaft 22 and leaf 24 is shown. The shaft 22 is generally comprised of a suitable material such as metal or plastic. A center portion 40 of the shaft 22 is relatively straight with a distal end 42 of the shaft being slightly curved. The cross-sectional shape of the shaft 22, in this embodiment, is generally oval having a flat first side 44 and a flat second side 46. In this embodiment, three internal passages 48 are provided in the shaft 22 to act as a working channel and housings for an illumination fiber optic bundle and an image fiber optic bundle. Mounted on the first side 44 of the shaft 22, in this embodiment, are two posts 50, 51. The posts 50, 51 may be formed integrally with the shaft 22 or maybe fixedly mounted thereto. The posts 50, 51 in this embodiment, are virtually identical to each other with each post having an enlarged head 52 and a relatively narrow neck 54.

The leaf 24 is also generally comprised of a suitable material such as metal or plastic and is provided for interaction with the tongue of a patient. The interaction might include either moving the tongue or depressing the tongue. The leaf 24, in this embodiment, has a first section 56 that is relatively straight and a second section 58 that is relatively curved. The second section 58 also comprises a leaf tip 60. The first section 56 of the leaf, in this embodiment, is provided with two button holes or notches 62, 63. Each of the button holes 62, 63, in this embodiment, generally comprise a first type of aperture 64 suitably sized and shaped for the passage of the post heads 52 therein. The button holes 62, 63 also comprise a second type of aperture 65 that is smaller in size than the first type of aperture 64 proximate a first side 66 of the leaf, but which has the same size as the first type of aperture 64 in the interior of the leaf and thus forms a type of ledge. In this embodiment, the button holes 62, 63 do not pass through the entire thickness of the leaf 24 such that a second side 68 of the leaf has a relatively continuous surface. However, in an alternative embodiment the posts may pass entirely through the thickness of the leaf 24. In addition, any suitable number, size or shape of posts can be provided. The second side 68 of the leaf may be smooth or textured depending on the desired degree of interaction with a patient's tongue. In the embodiment shown, the second type of apertures 65 are suitably sized and shaped to receive the necks 54 of the posts 50, 51 therein. Preferably, the second types of apertures 65 are tapered proximate the first side 66 of the leaf such that a scabbard type fit is provided between the necks 54 and second type of apertures 65. The position of the button holes 62, 63 on the leaf 24 is provided such that the posts 50, 51 on the shaft 22 can be inserted into the first type of apertures 64 of the button holes 62, 63, respectively. The first side of the leaf 66 would thus be located proximate the first side 44 of the stem 22. The second section 58 of the leaf 24, at this first position, would be slightly separated from the curved distal end 42 of the shaft.

Figure 3:
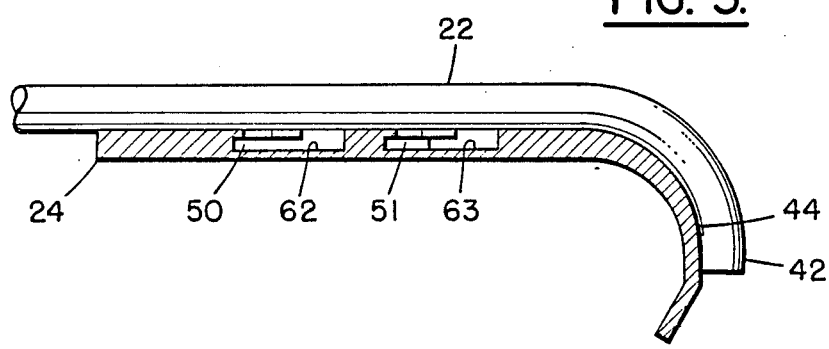
FIG. 3 is a cross-sectional side view of the leaf mounted to the stem of the blade shown in FIG. 1.

Referring also to FIG. 3, the assembled position of the blade section is shown. From the first position described above the leaf 24 can be moved forward towards the distal end 42 of the shaft suc that the second section 58 of the leaf 24 comes to rest on the first side 44 of the distal end 42. The button holes 62, 63 are moved forward such that the second type of apertures 65 are advanced around the posts 50, 51 and cooperate therewith to prevent separation of the leaf 24 from the shaft 22 without first moving the leaf 24 back to the first position.

The reduced size of the second type of aperture 65 or ledge formed thereby prevents the heads 52 of the posts from being pulled out through the second type of apertures 65. In addition, the tapered shape of the second type of apertures 65 proximate the first side 66 of the leaf 24 scabbards the posts 50, 51. The leaf 24 and stem 22 thus assembled, the leaf 24 is relatively fixedly held to the stem 22 at the second position as shown in FIG. 3. The leaf 24 can nonetheless be removed from the stem 22 by moving the leaf to the first position and then removing the leaf 24 from the stem 22 with the posts 50, 51 exiting the first type of apertures 64 of the button holes 62, 63. With the use of the removable leaf as described above, different types of leafs can be used with the laryngoscope 10. This is particularly applicable for varying the features of the desired leaf such as the width, length, tip size and shape and surface texture or smoothness of the leaf without having to provide an entirely different blade. Wide leafs can be used for patients with enlarged tongues. Small leafs can be used for patients with small tongues. Leafs with smooth surfaces can be used if retraction of the tongue is not necessary. Leafs with textured surfaces can be used if retraction of the tongue is desired. Obviously, with the present invention a single laryngoscope can be used for variously different patients by merely interchanging the leaf.

Although the above embodiment has been described in detail, it is apparent that various alternate embodiments may be devised by those skilled in the art. Any suitable mounting means could be used between the stem and leaf of the blade. Any suitably mountable leaf could be used with a suitable stem and the leafs could be used with any suitable type of instrument. Additional mounting or retaining means could also be provided.

It should be understood that the foregoing description is only illustrative of the invention. Various alternatives and modifications can be devised by those skilled in the art without departing from the scope of the invention. Accordingly, the present invention is intended to embrace all of such alternatives, modifications and variances which fall within the scope of the appended claims.

What is claimed is:

1. An instrument for accessing a target area including a blade, the blade comprising:
    shaft means positionable proximate the target area of a patient, said shaft means having a relatively curved distal section for cooperatingly supporting a distal section of a leaf means thereon and at least one fiber optic image bundle for viewing a target area; and 2. A laryngoscope comprising:
    blade means having a shaft means with an image bundle for viewing a target area, a distal end positionable proxmiate the throat region of a patient, and a leaf means interactable with the tongue of a patient, said leaf means having a notch means; and
    means for removable mounting said leaf means with said shaft means such that said leaf means is positionable proximate said shaft means distal end, said mounting means including a post means fixed to said shaft means cooperatable with said notch means on said leaf means, said notch means comprising a first type of aperture means and a second type of aperture means, said second type of aperture means being relatively tapered from said first type of aperture means for providing a scabbard fit between said second type of aperture means and said post means whereby said leaf means can be removed from said shaft means.

3. A laryngoscope as in claim 2 wherein said first type of aperture means has a first size for insertion of said post means therein.

4. A laryngoscope as in claim 2 wherein said leaf means comprises a relatively curved section.

5. A laryngoscope as in claim 2 wherein said leaf means comprises a first side having a textured surface.

6. A laryngoscope as in claim 2 wherein said leaf means comprises a relatively wide section for interaction with the tongue of a patient.

7. A laryngoscope as in claim 2 wherein said leaf means is movable relative to said shaft means between a first position and a second position.

8. A laryngoscope as in claim 7 wherein said second position comprises said leaf means being relatively fixed with said shaft means.

9. A method of manufacturing a laryngoscope comprising the steps of:
    providing an elongate shaft means being positionable proximate a throat region of a patient, said shaft means having a relatively curved distal section;
    inserting an image bundle into a channel in said shaft means;
    fixing a post means on one side of said shaft means;
    providing a leaf means having a slot means cooperatable with said post means on said shaft means, said slot means having tapered bayonet aperture means for making a scabbard fit with said post means, said leaf means further including a relatively curved distal section for cooperation with said shaft means distal section whereby said leaf means can be connected to and removed from said shaft means.

* * * * *

UNITED STATES PATENT AND TRADEMARK OFFICE
CERTIFICATE OF CORRECTION

PATENT NO. : 4,947,829

DATED : August 14, 1990

INVENTOR(S) : Bullard

It is certified that error appears in the above-identified patent and that said Letters Patent is hereby corrected as shown below:

Claim 1, Col. 6, line 3, after "and insert the following:

--means for removably mounting a leaf means with said shaft means comprising at least one post fixed to said shaft means having a neck portion and an enlarged head portion for cooperating with a slot in the leaf means whereby different types of leaf means can be used with the instrument.--

Claim 2, Col. 6, line 9, delete "removable" and insert --removably--.

Signed and Sealed this

Seventh Day of January, 1992

Attest:

HARRY F. MANBECK, JR.

*Attesting Officer*  *Commissioner of Patents and Trademarks*